United States Patent … US 11,163,057 B2
Iizuka et al. … Nov. 2, 2021

(54) ESTIMATION DEVICE, LIVING BODY COUNT ESTIMATION DEVICE, ESTIMATION METHOD, AND RECORDING MEDIUM

(71) Applicant: PANASONIC INTELLECTUAL PROPERTY MANAGEMENT CO., LTD., Osaka (JP)

(72) Inventors: Shoichi Iizuka, Osaka (JP); Takeshi Nakayama, Hyogo (JP); Naoki Honma, Iwate (JP); Nobuyuki Shiraki, Iwate (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 417 days.

(21) Appl. No.: 16/389,541

(22) Filed: Apr. 19, 2019

(65) Prior Publication Data

US 2019/0339379 A1 Nov. 7, 2019

(30) Foreign Application Priority Data

May 2, 2018 (JP) .............................. JP2018-088490
Jan. 16, 2019 (JP) .............................. JP2019-005577

(51) Int. Cl.
*G06K 9/00* (2006.01)
*G01S 13/88* (2006.01)
(Continued)

(52) U.S. Cl.
CPC .............. *G01S 13/88* (2013.01); *G01S 13/04* (2013.01); *G01S 13/426* (2013.01); *H04L 12/00* (2013.01);
(Continued)

(58) Field of Classification Search
CPC ........ G01S 13/88; G01S 7/354; G01S 13/003; G01S 13/32; G01S 7/418; G01S 13/426;
(Continued)

(56) References Cited

U.S. PATENT DOCUMENTS

2010/0019954 A1  1/2010  Mizutani et al.
2017/0205502 A1* 7/2017  Honma ................... G01S 13/42
2018/0011169 A1  1/2018  Nakayama et al.

FOREIGN PATENT DOCUMENTS

JP      2009-150722    7/2009
JP          5025170    9/2012
(Continued)

*Primary Examiner* — Stephen P Coleman
(74) *Attorney, Agent, or Firm* — Greenblum & Bernstein, P.L.C.

(57) ABSTRACT

An estimation device includes: a living body information extraction unit that extracts living body information which is a component corresponding to one or more living bodies in a space; an eigenvector calculation unit that calculates one or more eigenvectors of a living body correlation matrix obtained from the living body information; a first position estimation unit that estimates, using the living body correlation matrix, positions of the one or more living bodies and at least one false image, according to a predetermined position estimation method; a second steering vector output unit that extracts, from first steering vectors stored in a storage, and outputs as second steering vectors, first steering vectors corresponding to the positions estimated; and a second position estimation unit that estimates at least one of the position and the number of the one or more living bodies, using the one or more eigenvectors and the second steering vectors.

12 Claims, 12 Drawing Sheets

(51) Int. Cl.
*G01S 13/42* (2006.01)
*G01S 13/04* (2006.01)
*H04L 12/00* (2006.01)
G06T 7/246 (2017.01)
G06F 3/00 (2006.01)
A61B 5/0245 (2006.01)

(52) U.S. Cl.
CPC .............. *A61B 5/0245* (2013.01); *G06F 3/00* (2013.01); *G06K 9/00362* (2013.01); *G06K 9/00771* (2013.01); *G06T 7/246* (2017.01); *G06T 2207/10028* (2013.01); *G06T 2207/30196* (2013.01); *G06T 2207/30242* (2013.01)

(58) Field of Classification Search
CPC ......... G01S 13/04; H04L 12/00; G06T 7/246; G06T 2207/10028; G06T 2207/30242; G06T 2207/30196; G06K 9/00362; G06K 9/00771; G06F 3/00; A61B 5/0245
USPC ...................................................... 382/103
See application file for complete search history.

(56) References Cited

FOREIGN PATENT DOCUMENTS

| | | |
|---|---|---|
| JP | 5047002 | 10/2012 |
| JP | 5116590 | 1/2013 |
| JP | 5519132 | 6/2014 |
| JP | 2014-228291 | 12/2014 |
| JP | 2015-072173 | 4/2015 |
| JP | 2015-117972 | 6/2015 |
| JP | 2018-008021 | 1/2018 |

* cited by examiner

FIG. 3

| | $u_1$ | $u_2$ | $u_3$ | ... | $P_{peaki}$ |
|---|---|---|---|---|---|
| $a_{peak1}$ | 0.05 | 0.9 | 0.01 | ... | 0.9 |
| $a_{peak2}$ | 0.83 | 0.1 | 0.02 | ... | 0.83 |
| $a_{peak3}$ | 0.14 | 0.1 | 0.11 | ... | 0.14 |
| ... | ... | ... | ... | | ... |

ESTIMATED POSITION DISTRIBUTION
ACCORDING TO Capon METHOD

ESTIMATED POSITION DISTRIBUTION
IN WORKING EXAMPLE

US 11,163,057 B2

ESTIMATION DEVICE, LIVING BODY COUNT ESTIMATION DEVICE, ESTIMATION METHOD, AND RECORDING MEDIUM

CROSS REFERENCE TO RELATED APPLICATION

This application claims the benefit of priority of Japanese Patent Application Number 2018-088490 filed on May 2, 2018 and Japanese Patent Application Number 2019-005577 filed on Jan. 16, 2019, the entire contents of which are hereby incorporated by reference.

BACKGROUND

1. Technical Field

The present disclosure relates to an estimation device, a living body count estimation device, an estimation method, and a recording medium, and particularly relates to an estimation device, a living body count estimation device, an estimation method, and a recording medium for estimating at least the positions or the number of living bodies by using radio signals.

2. Description of the Related Art

Techniques for detecting a detection target by using wirelessly transmitted signals are being developed (see Japanese Unexamined Patent Application Publication No. 2015-117972 (Patent Literature (PTL) 1), for example.

PTL 1 discloses a technique capable of finding out the number and positions of persons who are detection targets, by analyzing eigenvalues of components including a Doppler effect using Fourier transform on signals received wirelessly.

SUMMARY

However, in the technique disclosed in PTL 1, in a situation where the difference between magnitudes of eigenvalues corresponding to living bodies decreases, such as when the number of living bodies which are the detection targets is large, there is the problem that the estimation accuracy for the number of living bodies which are the detection targets deteriorates, and living body position estimation accuracy deteriorates.

The present disclosure is conceived in view of the aforementioned circumstances and has an object to provide an estimation device, a living body count estimation device, an estimation method, and a recording medium capable of accurately estimating at least the positions or the number of living bodies by using radio signals.

In order to achieve the aforementioned object, an estimation device, etc., according to an aspect of the present disclosure includes: a living body information extraction unit configured to extract, from a reception signal obtained by receiving a signal transmitted to a predetermined space, living body information which is a component corresponding to one or more living bodies present in the predetermined space; an eigenvector calculation unit configured to calculate one or more eigenvectors of a living body correlation matrix obtained from the living body information; a first position estimation unit configured to estimate, using the living body correlation matrix, positions including a position of each of the one or more living bodies and a position of at least one false image, according to a predetermined position estimation method; a second steering vector output unit configured to extract, from among a plurality of first steering vectors stored in advance in a storage, first steering vectors corresponding to the positions estimated by the first position estimation unit, and output the first steering vectors as second steering vectors; and a second position estimation unit configured to estimate at least one of the position of each of the one or more living bodies and a total number of the one or more living bodies, using the one or more eigenvectors and the second steering vectors.

According to the estimation device, etc., according to the present disclosure, at least the positions or the number of living bodies can be accurately estimated.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

FIG. 3 is a table showing an example of a result of calculating correlations and evaluation functions of second steering vectors and eigenvectors according to Embodiment 1;

Figure 1:
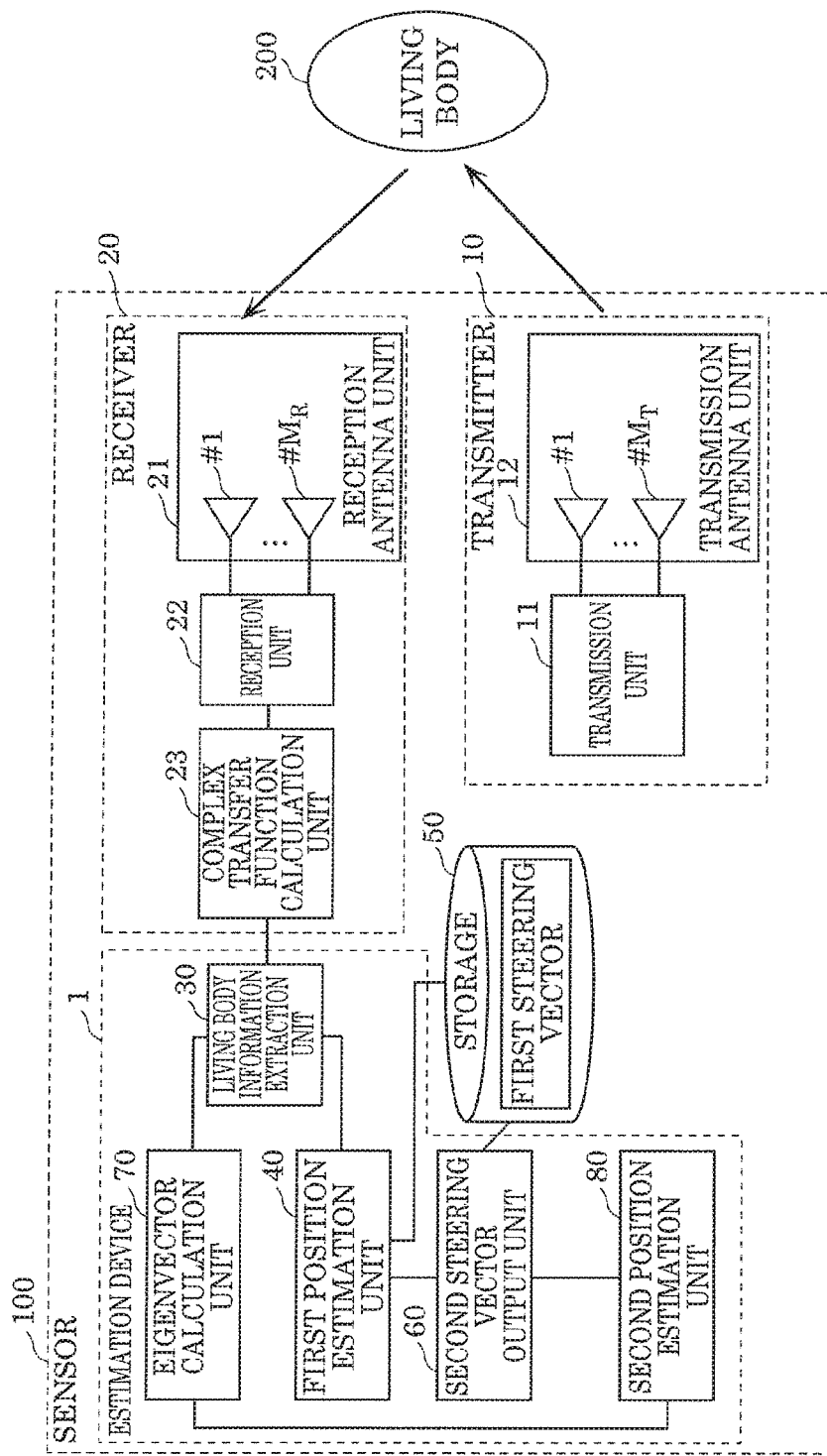
FIG. 1 is a block diagram illustrating a configuration of a sensor according to Embodiment 1.

DETAILED DESCRIPTION OF THE EMBODIMENT (Underlying Knowledge Forming the Basis of the Present Disclosure)

Techniques which detect detection targets by using wirelessly transmitted signals are being developed (see PTL 1, Japanese Unexamined Patent Application Publication No. 2014-228291 (PTL 2), Japanese Patent Publication No. 5047002 (PTL 3), and Japanese Patent Publication No. 5025170 (PTL 4), for example).

For example, PTL 1 discloses a technique of detecting the number and positions of persons who are detection targets, by analyzing eigenvalues of components including a Doppler effect, using Fourier transform. Specifically, Fourier transform is performed on reception signals, an autocorrelation matrix is calculated for a waveform obtained by extracting a specific frequency component, and eigenvalue decomposition is performed on the autocorrelation matrix to calculate eigenvalues. In general, an eigenvalue and an eigenvector indicate a propagation path of radio waves transmitted from a transmission antenna unit to a reception antenna unit, that is, one of paths. Under ordinary circumstances, there are various paths such as a direct wave, reflection derived from a fixed object such as a wall, etc., and the paths respectively correspond to eigenvectors and eigenvalues. However, in the technique in PTL 1, a component that does not include living body information is removed, and thus only a path obtained by reflection by a living body and a path corresponding to noise are indicated in the eigenvalues and eigenvectors. Here, since the value of an eigenvalue corresponding to a noise is smaller than the value of an eigenvalue corresponding to a living body, the number of living bodies can be estimated by counting the number of eigenvalues larger than a predetermined threshold, among the eigenvalues.

However, in the technique disclosed in PTL 1, when the target living body is far or when the number of living bodies is large, the difference between the eigenvalues corresponding to the living body and the eigenvalues corresponding to noise is reduced, and thus there is the problem that person count estimation accuracy deteriorates. This is because, in a situation where the Doppler effect is extremely weak, it becomes difficult to detect a weak signal exhibiting a Doppler shift, due to the influence of internal noise of the receiver, interference waves coming from sources other than the detection target, and the presence of a body generating a Doppler effect other than the detection target.

PTL 2 discloses a technique of estimating the position of a target by using a direction estimation algorithm such as the multiple signal classification (MUSIC) method. Specifically, in a reception station that has received signals emitted by a transmission station, Fourier transform is performed on the reception signals, an autocorrelation matrix is calculated for a waveform obtained by extracting a specific frequency component, and a direction estimation algorithm such as the MUSIC method is applied to the autocorrelation matrix. This enables accurate living body direction estimation. However, since the MUSIC method used in PTL 2 is a method of determining the direction of a living body position by using the number of living bodies, which are the detection targets, that is assumed to be known in advance, and thus estimating the number of living bodies is not possible.

Furthermore, for example, PTL 3 discloses a technique of estimating the number of arriving waves, that is, the number of transmitters such as cellular phones, from the correlation between the eigenvectors of reception signals received by a plurality of antennas and the steering vectors in a range where radio waves can arrive.

Furthermore, for example, PTL 4 discloses a technique of assuming various numbers of arriving waves for reception signals received by a plurality of antennas, calculating evaluation functions using steering vectors for the number of arriving waves, and estimating, as the true number of arriving waves, the number of arriving waves having a maximum evaluation function.

However, the techniques disclosed in PTL 3 and PTL 4 are techniques for estimating the number of transmitters emitting the radio waves, and estimating the number of living bodies is not possible.

The inventors arrived at conceiving a detecting device (a sensor) capable of accurately detecting at least the positions or the number of living bodies by using radio signals, and without having the target living bodies carry a special device such as a transmitter, etc.

Specifically, an estimation device according to an aspect of the present disclosure includes: a living body information extraction unit configured to extract, from a reception signal obtained by receiving a signal transmitted to a predetermined space, living body information which is a component corresponding to one or more living bodies present in the predetermined space; an eigenvector calculation unit configured to calculate one or more eigenvectors of a living body correlation matrix obtained from the living body information; a first position estimation unit configured to estimate, using the living body correlation matrix, positions including a position of each of the one or more living bodies and a position of at least one false image, according to a predetermined position estimation method; a second steering vector output unit configured to extract, from among a plurality of first steering vectors stored in advance in a storage, first steering vectors corresponding to the positions estimated by the first position estimation unit, and output the first steering vectors as second steering vectors; and a second position estimation unit configured to estimate at least one of the position of each of the one or more living bodies and a total number of the one or more living bodies, using the one or more eigenvectors and the second steering vectors.

According to this configuration, it is possible to combine the two mutually different estimation methods of a method that uses eigenvectors instead of eigenvalues and a predetermined position estimation method such as the Capon method, and thus it is possible to accurately estimate at least the positions or the number of living bodies, by using radio signals. It should be noted that in the present Specification, the positions of living bodies indicated in position estimation are referred to as images, and among the images, an image that does not correspond to a position of a living body that is actually present is defined as a false image, and an image that corresponds to a position of a living body that is actually present is defined as an actual image.

Here, for example, the second position estimation unit is configured to calculate a product or a correlation of the one or more eigenvectors and the second steering vectors, and estimate, as the position, a position indicated by eigenvectors or second steering vectors of which the product or the correlation calculated is a value greater than or equal to a threshold, among the one or more eigenvectors and the second steering vectors.

Accordingly, the positions of living bodies can be accurately estimated using radio signals.

Furthermore, for example, the second position estimation unit is configured to estimate, as the total number, a total number of eigenvectors or second steering vectors of which the product or the correlation calculated is a value greater than or equal to a threshold, among the one or more eigenvectors and the second steering vectors.

Accordingly, the number of living bodies can be accurately estimated using radio signals.

Here, for example, the predetermined position estimation method may be a Capon method, or the predetermined position estimation method may be a Beamformer method Accordingly, a position estimation method such as the Capon method which can be used even when the number of persons (also referred to here as person count) is unknown, though having poor position estimation accuracy, is combined with a method that uses eigenvalues, thereby enabling at least the positions or the number of living bodies to be estimated accurately using radio signals.

Furthermore, for example, the first position estimation unit may include an advance person count estimation unit configured to estimate a person count including the total number of the one or more living bodies and a total number of the at least one false image, using eigenvalues of the living body correlation matrix, and the predetermined position estimation method may be a multiple signal classification (MUSIC) method that uses the person count estimated by the advance person count estimation unit.

Accordingly, a position estimation method which uses the MUSIC method, for which an already-known person count is a prerequisite, by preestimating a person count for the time being using eigenvalues and setting this inaccurate and false image-inclusive person count as the already-known person count, is combined with a method that uses eigenvalues, to thereby enable at least the positions or the number of living bodies to be estimated accurately using radio signals.

Here, for example, the estimation device further includes: a transmitter including N transmission antenna elements, where N is a natural number greater than or equal to 2; and a receiver including M reception antenna elements, where M is a natural number greater than or equal to 2, and a transfer function calculation unit configured to calculate, from reception signals received by each of the M reception antenna elements during a predetermined period, a plurality of complex transfer functions indicating a propagation characteristic between the N transmission antenna elements and the M reception antenna elements, wherein the eigenvector calculation unit is configured to calculate the living body correlation matrix from the variation component in each of the M reception antenna elements extracted by the living body information extraction unit, and calculate the one or more eigenvectors of the living body correlation matrix calculated.

Furthermore, a living body count estimation device according to an aspect of the present disclosure includes: a plurality of estimation devices each being the estimation device in the foregoing aspect; an estimated position distribution calculation unit configured to calculate, based on a position of each of one or more living bodies present in each of predetermined spaces that is estimated by a corresponding one of the plurality of estimation devices, an estimated position distribution for a total space including the predetermined spaces which partially overlap each other; and a living body count estimation unit configured to estimate a living body count which is a total number of one or more living bodies present in the total space, using the total number of the one or more living bodies present in each of the predetermined spaces estimated by the corresponding one of the plurality of estimation devices.

According to this configuration, it is possible to cause a plurality of transmission stations and reception stations to operate together by using a plurality of estimation devices, and thus the range over which person count estimation is possible can be increased.

Here, for example, the living body count estimation unit may be configured to estimate, as the living body count, a total number of local minimums of a dispersal of the positions estimated by the plurality of estimation devices, or the living body count estimation unit may be configured to estimate, as the living body count, a total number of maximum values of a density of the positions estimated by the plurality of estimation devices.

According to this configuration, the same living body estimated overlappingly by a plurality of estimation devices can be counted as a single living body, the range over which accurate estimation is possible can be increased.

Furthermore, an estimation method according to an aspect of the present disclosure includes: extracting, from a reception signal obtained by receiving a signal transmitted to a predetermined space, living body information which is a component corresponding to one or more living bodies present in the predetermined space; calculating one or more eigenvectors of a living body correlation matrix obtained from the living body information; estimating, using the living body correlation matrix, positions including a position of each of the one or more living bodies and a position of at least one false image, according to a predetermined position estimation method; extracting, from among a plurality of first steering vectors stored in advance in a storage, first steering vectors corresponding to the positions estimated in the estimating of the positions, and outputting the first steering vectors as second steering vectors; and estimating at least one of the position of each of the one or more living bodies and a total number of the one or more living bodies, using the one or more eigenvectors and the second steering vectors.

Furthermore, a recording medium according to an aspect of the present disclosure is a non-transitory computer-readable recording medium having recorded thereon a program for causing a computer to execute: extracting, from a reception signal obtained by receiving a signal transmitted to a predetermined space, living body information which is a component corresponding to one or more living bodies present in the predetermined space; calculating one or more eigenvectors of a living body correlation matrix obtained from the living body information; estimating, using the living body correlation matrix, positions including a position of each of the one or more living bodies and a position of at least one false image, according to a predetermined position estimation method; extracting, from among a plurality of first steering vectors stored in advance in a storage, first steering vectors corresponding to the positions estimated in the estimating of the positions, and outputting the first steering vectors as second steering vectors; and estimating at least one of the position of each of the one or more living bodies and a total number of the one or more living bodies, using the one or more eigenvectors and the second steering vectors.

It should be noted that the present disclosure can be implemented, not only as an apparatus (device), but also as an integrated circuit including the processing units included in such an apparatus, a method having, as steps, the processing units included in such apparatus, a program which causes a computer to execute such steps, and information, data, or a signal representing such program. Moreover, such program, information, data and signal may be distributed via a recording medium such as a CD-ROM or a communication network such as the Internet.

Hereinafter, exemplary embodiments of the present disclosure will be described in detail with reference to the Drawings. It should be noted that each of the exemplary embodiments described hereinafter illustrate a specific example of the present disclosure. The numerical values, shapes, materials, structural components, the arrangement and connection of the structural components, steps, the processing order of the steps, etc., shown in the following exemplary embodiments are mere examples, and are therefore not intended to limit the present disclosure. Furthermore, among the structural components in the following exemplary embodiments, components not recited in any one of the independent claims defining the most generic concept of the present disclosure are described as optional components making up a more preferable form. It should be noted that in the Specification and the Drawings, structural components having substantially the same functional configuration are given the same numerical sign in order to omit overlapping descriptions.

Embodiment 1

Hereinafter, an estimation method performed by sensor 100, etc., according to Embodiment 1 will be described with reference to the Drawings.

[Configuration of Sensor 100]

Figure 2:
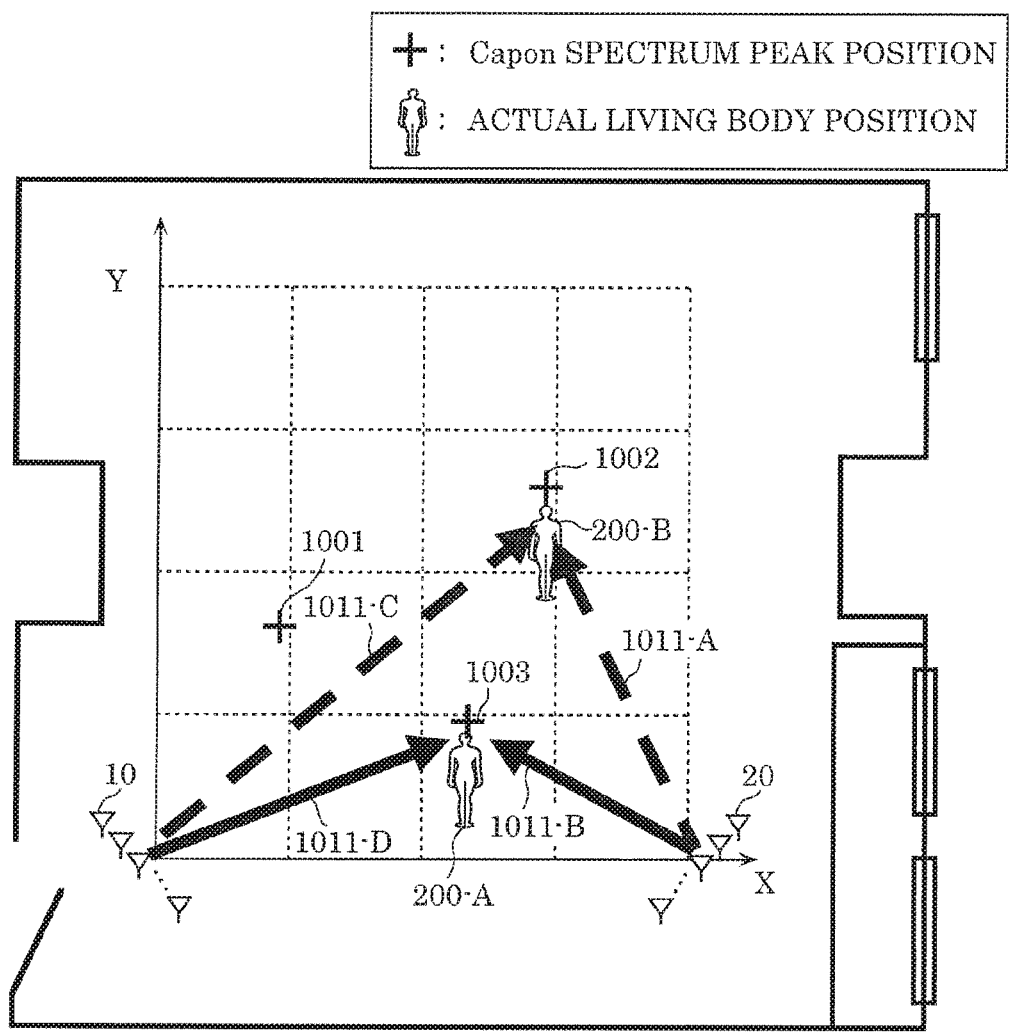
FIG. 2 is a diagram illustrating an example of an arrangement of a transmitter and a receiver, and a concept of a position estimation method performed by an estimation device.

FIG. 1 is a block diagram illustrating the configuration of sensor 100 according to Embodiment 1. FIG. 2 is a diagram illustrating an example of the arrangement of transmitter 10 and receiver 20, and the concept of the position estimation method performed by estimation device 1, according to Embodiment 1. Sensor 100 illustrated in FIG. 1 includes estimation device 1, transmitter 10, receiver 20, living body information extraction unit 30, and storage 50. Hereinafter, the detailed configuration will be described.

[Transmitter 10]

Transmitter 10 includes N transmission antenna elements (N is a natural number greater than or equal to 2). Specifically, as illustrated in FIG. 1, transmitter 10 includes transmission unit 11 and transmission antenna unit 12 including an array antenna having $M_T$ elements. Here, $M_T$ elements corresponds to N transmission antenna elements (N is a natural number greater than or equal to 2), and $M_T$ is a natural number greater than or equal to 2.

(Transmission Antenna Unit 12)

Transmission antenna unit 12 includes a transmission array antenna having $M_T$ elements. Here, the transmission array antenna having $M_T$ elements corresponds to N transmission antenna elements, and $M_T$ is a natural number greater than or equal to 2.

Transmission antenna unit 12 transmits high-frequency signals generated by transmission unit 11.

(Transmission Unit 11)

Transmission unit 11 generates a high-frequency signal used for estimating the presence or absence, position and/or number of living body 200. For example, transmission unit 11 generates a continuous wave (CW), and the generated CW is transmitted as a transmission wave, from transmission antenna unit 12. It should be noted that the signal generated is not limited to a sinusoidal signal such as CW, and may be a modulated signal (modulated wave signal).

[Receiver 20]

Receiver 20 includes M reception antenna elements (M is a natural number greater than or equal to 2), and complex transfer function calculation unit 23. Specifically, as illustrated in FIG. 1, receiver 20 includes reception antenna unit 21, reception unit 22, and complex transfer function calculation unit 23.

(Reception Antenna Unit 21)

Reception antenna unit 21 includes a reception array antenna having $M_R$ elements. Here, the reception array antenna having $M_R$ elements corresponds to M reception antenna elements, and $M_R$ is a natural number greater than or equal to 2. Reception antenna unit 21 receives high-frequency signals using the reception array antenna.

(Reception Unit 22)

Reception unit 22 converts, by using for example a downconverter or the like, the high-frequency signals received by reception antenna unit 21 into low-frequency signals on which signal processing is possible. Reception unit 22 transmits the low-frequency signals obtained from the conversion to complex transfer function calculation unit 23.

It should be noted that, although transmitter 10 and receiver 20 are adjacent to each other in FIG. 1, the configuration is not limited to such. For example, as illustrated in FIG. 2, transmitter 10 and receiver 20 may be disposed at distant positions.

Furthermore, although in FIG. 1 the transmission array antenna used by transmitter 10 and the reception array antenna used by receiver 20 are disposed at different positions as different units, the configuration is not limited to such. The transmission array antenna and the reception array antenna used by transmitter 10 and receiver 20 may be a shared array antenna. In addition, transmitter 10 and receiver 20 may be used in common with radio equipment hardware such as a Wi-Fi (registered trademark) router or extension unit.

(Complex Transfer Function Calculation Unit 23)

Complex transfer function calculation unit 23 is an example of a transfer function calculation unit, and calculates, based on the reception signals respectively received by the M reception antenna elements during the predetermined period, a plurality of complex transfer functions each representing propagation characteristics between each of possible pairs of the N transmission antenna elements and the M reception antenna elements.

More specifically, complex transfer function calculation unit 23 calculates, based on signals measured by the reception array antenna of reception antenna unit 21, complex transfer functions each representing propagation characteristics between the reception array antenna and the transmission array antenna of transmission antenna unit 12. In the present embodiment, complex transfer function calculation unit 23 calculates complex transfer functions each representing propagation characteristics between the $M_T$ transmission antenna elements of transmission antenna unit 12 and the $M_R$ reception antenna elements of reception antenna unit 21, based on the low-frequency signals transmitted from reception unit 22.

It should be noted that there are cases where the complex transfer functions calculated by complex transfer function calculation unit 23 include reflected waves and/or dispersed waves which are signals generated when part of the transmission waves transmitted from transmission antenna unit 12 is reflected or dispersed by living body 200. Furthermore, the complex transfer functions calculated by complex transfer function calculation unit 23 include reflected waves that did not come via living body 200, such as direct waves from transmission antenna unit 12 and reflected waves derived from fixed objects. Furthermore, the amplitude and phase of the signals reflected or dispersed by living body 200, that is, the reflected waves and the dispersed waves that came via living body 200 vary constantly due to living body activity such as respiration and heartbeat, etc. Hereinafter, description will be carried out under the assumption that the complex transfer functions calculated by complex transfer function calculation unit 23 include reflected waves and dispersed waves which are the signals reflected or dispersed by living body 200.

[Estimation Device 1]

Estimation device 1 accurately estimates, using radio signals, at least the positions or the number of living bodies by combining a position estimation method which can be used even when the number of persons (also referred to here as person count) is unknown, such as the Capon method, and a position estimation method which uses eigenvalues. In the present embodiment, as illustrated in FIG. 1, estimation device 1 includes living body information extraction unit 30, first position estimation unit 40, second steering vector output unit 60, eigenvector calculation unit 70, and second position estimation unit 80. It should be noted that estimation device 1 may include storage 50. Furthermore, estimation device 1 may include transmitter 10 and receiver 20 although inclusion of transmitter 10 and receiver 20 is not essential. Hereinafter, the detailed configuration of estimation device 1 will be described.

(Living Body Information Extraction Unit 30)

Living body information extraction unit 30 extracts, from a reception signal obtained by receiving a signal transmitted to a predetermined space, living body information which is a component corresponding to one or more living bodies present in the predetermined space. More specifically, living body information extraction unit 30 extracts, as living body information, a variation component in each of the M reception antenna elements, which is caused by the influence of a living body, from the complex transfer functions calculated by complex transfer function calculation unit 23.

In the present embodiment, living body information extraction unit 30 extracts, from a signal measured by the reception array antenna of reception antenna unit 21, a living body component which is a signal component which was transmitted from the transmission array antenna of transmission antenna unit 12 and reflected or dispersed by one or more living bodies 200.

More specifically, living body information extraction unit 30 records the complex transfer functions calculated by complex transfer function calculation unit 23, in chronological order which is the order in which the signals are measured. Then, living body information extraction unit 30 extracts the variation component caused by the influence of living body 200, among changes of complex transfer functions recorded in chronological order. Hereinafter, the variation component of complex transfer functions caused by the influence of living body 200 will be referred to as a living body component or living body information.

Methods for extracting the living body component include, for example, a method of extracting only a living body component after transformation to a frequency region by Fourier transform, or the like, or a method of extraction by calculating the difference between complex transfer functions at two different times. These methods remove the components of a direct wave and a reflected wave that came via a fixed object, and thus only the living body components that came via living body 200 remain.

It should be noted that, since there are $M_T$ of the transmission antenna elements included in the transmission array antenna and $M_R$ of the reception antenna elements included in the reception array antenna, that is, there are a plurality of both antenna elements in the present embodiment, the living body components coming via living body 200 of the complex transfer functions corresponding to the transmission and reception array antennas are also plural in number. Hereinafter, a matrix into which these living body components are compiled is referred to as living body channel matrix H(t).

In this manner, living body information extraction unit 30 calculates living body channel matrix H(t) from the chronological complex transfer functions. Furthermore, living body information extraction unit 30 outputs living body channel matrix H(t) obtained from the extracted living body components to first position estimation unit 40 and eigenvector calculation unit 70.

(Eigenvector Calculation Unit 70)

Eigenvector calculation unit 70 calculates one or more eigenvectors of a living body correlation matrix obtained from living body information. More specifically, eigenvector calculation unit 70 calculates a living body correlation matrix from the living body information, which is the variation component of each of the M reception antenna elements, extracted by living body information extraction unit 30, and extracts the eigenvectors of the calculated living body correlation matrix.

In the present embodiment, eigenvector calculation unit 70 calculates, according to Equation 1, correlation matrix R from living body channel matrix H(t) received from living body information extraction unit 30. In Equation 1, $E[\cdot]$ represents an ensemble average, and $\{\cdot\}^H$ represents complex conjugate transposition Correlation matrix R is an example of the aforementioned living body correlation matrix.

[Math. 1]

$$R = E[H^H(t)H(t)] \qquad \text{Equation 1}$$

Furthermore, eigenvector calculation unit 70 transmits the eigenvectors obtained by eigenvector decomposition of the calculated correlation matrix R to second position estimation unit 80. Here, eigenvalue decomposition of correlation matrix R of living body channel matrix H(t) can be expressed using Equations 2 to 4 below. It should be noted that, in Equation 3, $u_1$ to $u_N$ represent eigenvectors having an element count of N. In Equation 4, $\lambda_1$ to $\lambda_N$ represent eigenvalues corresponding to the eigenvectors.

[Math. 2]

$$R = U\Lambda U \qquad \text{Equation 2}$$

[Math. 3]

$$U = [u_1, u_2, \ldots, u_N] \qquad \text{Equation 3}$$

[Math. 4]

$$\Lambda = \text{diag}[\lambda_1, \lambda_2, \ldots, \lambda_N] \qquad \text{Equation 4}$$

Here, the concept of the eigenvectors to be calculated will be described with reference to FIG. 2. It is assumed that eigenvector calculation unit 70 calculates eigenvectors 1011-A to eigenvector 1011-D, from living body channel matrix H(t) obtained in a space where living body 200-A and living body 200-B are present, as illustrated in FIG. 2 for example. In this case, the calculated eigenvector 1011-A and eigenvector 1011-C indicate the direction of living body 200-B as seen from a reception antenna of receiver 20 and a transmission antenna of transmitter 10, respectively. Furthermore, the calculated eigenvector 1011-B and eigenvector 1011-D indicate the direction of living body 200-A as seen from the reception antenna of receiver 20 and the transmission antenna of transmitter 10, respectively. This is because the eigenvectors calculated by eigenvector calculation unit 70 represent a path from the transmission antenna to the reception antenna, and thus correspond to vectors indicating the position of the living bodies which are the detection targets as seen from the transmission antenna and the reception antenna.

(Storage 50)

Storage 50 stores in advance a plurality of first steering vectors calculated in advance. Storage 50 is accessed by first position estimation unit 40 and second steering vector output unit 60 in order to refer to the stored first steering vectors.

Here, the method for calculating the first steering vectors will be described.

First, transmission-side first steering vector $a_t(\theta)$ representing the phase difference between respective antenna elements of the transmission array antenna is calculated at predetermined intervals in a predetermined range, according to Equation 5. For example, the transmission-side first steering vector can be calculated, according to Equation 5, at one-degree intervals from −45 degrees to 45 degrees with the forward direction from the transmission array antenna being set as 0 degrees.

[Math. 5]

$$a_t(\theta) = \left[1, e^{-j\frac{2\pi}{\lambda}d\sin\theta}, \ldots, e^{-j\frac{2\pi}{\lambda}d(N-1)\sin\theta}\right] \quad \text{Equation 5}$$

It should be noted that in Equation 5, $\lambda$ represents the wavelength, N represents the number of antenna elements included in the transmission array antenna, j represents the imaginary unit, and e represents the base of natural logarithm.

Next, in the same manner, reception-side first steering vector $a_r(\theta)$ representing the phase difference between respective antenna elements of the reception array antenna is calculated relative to a $\theta$ of transmission-side first steering vector $a_t(\theta)$.

[Math. 6]

$$a_r(\theta) = \left[1, e^{-j\frac{2\pi}{\lambda}d\sin\theta}, \ldots, e^{-j\frac{2\pi}{\lambda}d(M-1)\sin\theta}\right] \quad \text{Equation 6}$$

In Equation 6, $\lambda$ represents the wavelength, M represents the number of antenna elements included in the transmission array antenna, j represents the imaginary unit, and e represents the base of natural logarithm.

Then, the transmission-side first steering vector $a_t(\theta)$ and the corresponding reception-side first steering vector $a_r(\theta)$ are stored in storage 50 as first steering vectors.

(First Position Estimation Unit 40)

First position estimation unit 40 estimates positions of the one or more living bodies which includes one or more false images (also referred to here as false-image inclusive positions), using a living body correlation matrix obtained from living body information, according to the predetermined position estimation method. Here, the predetermined position estimation method is the Capon method but may be the beamformer method.

In the present embodiment, first position estimation unit 40 estimates one or more candidate positions of one or more living bodies 200 using living body channel matrix H(t) obtained from the living body components extracted by living body information extraction unit 30. First position estimation unit 40 estimates one or more candidate positions of one or more living bodies 200 using a position estimation method that can be used even when the number of living bodies is unknown, such as the beamformer method or the Capon method. It should be noted that, compared to a position estimation method which is performed under a situation in which the number of living bodies is already known, such as the MUSIC method, the beamformer method and the Capon method have poor accuracy and accurate person count estimation is not possible when used alone because false images are generated.

Hereinafter, the case of estimating one or more candidate positions of one or more living bodies 200 from living body channel matrix H(t), using the Capon method as an example of a position estimation method that can be used even when the number of living bodies is unknown will be described.

In the Capon method, first, an evaluation function $P_{Capon}$ corresponding to the power when the main lobe of directivity of the reception array antenna or the transmission array antenna is directed to a certain direction $\theta$, is calculated for every $\theta$ (referred to as Capon spectrum). Then, the direction $\theta$ in which the Capon spectrum is at a peak is estimated as the target direction.

The evaluation function $P_{Capon}$ used in the Capon method is indicated in Equation 7 below.

[Math. 7]

$$P_{capon} = \frac{1}{a^H(\theta)R^{-1}a(\theta)} \quad \text{Equation 7}$$

More specifically, by performing position estimation according to the Capon method from both the transmission array antenna of transmission antenna unit 12 and the reception array antenna of reception antenna unit 21, a two-dimensional Capon spectrum is created, and the position of the detected peak is estimated. It should be noted that, when detecting the peak, smoothing of the Capon spectrum may be performed in order to mitigate the influence of noise. Hereinafter, description is carried out assuming that $N_P$ peaks are detected.

Here, the concept of the living body position calculated according to the Capon method will be described using FIG. 2. FIG. 2 illustrates a diagram in which the position of the peak of a Capon spectrum estimated according to the Capon method by first position estimation unit 40 in the space in which living body 200-A and living body 200-B are present is superimposed on a coordinate system. Specifically, peak position 1001, peak position 1002, and peak position 1003 indicated by plus symbols represent the positions of peaks which are estimated by first position estimation unit 40. It should be noted that peak position 1001 is a position of a peak (hereafter also referred to as peak position) detected despite there being no living body present in actuality, and is a false image.

(Second Steering Vector Output Unit 60)

Second steering vector output unit 60 selects and outputs, as second steering vectors, first steering vectors corresponding to the false-image inclusive positions of the one or more living bodies which are estimated by first position estimation unit 40, among the plurality of first steering vectors stored in advance in storage 50.

In the present embodiment, second steering vector output unit 60 extracts, from among the first steering vectors calculated in advance stored in storage 50, first steering vectors corresponding to the $N_P$ peak positions (false-image inclusive living body positions) estimated by first position estimation unit 40. Specifically, second steering vector output unit 60 outputs, according to (Equation 5) and (Equation 6), $N_P$ first steering vectors corresponding to direction θ of peak positions seen from the transmission array antenna, which are received from first position estimation unit 40. It should be noted that in the present embodiment, in order to distinguish from the first steering vectors stored in storage 50, a first steering vector extracted by second steering vector output unit 60 will be referred to as a second steering vector and will be denoted as second steering vector $a_{peak}$.

(Second Position Estimation Unit 80)

Second position estimation unit 80 estimates at least the positions or the number of one or more living bodies, using the calculated eigenvectors and the outputted second steering vectors. Specifically, second position estimation unit 80 may calculate the product or the correlation of the calculated eigenvectors and the outputted second steering vectors, and estimate, as the positions of the living bodies, the positions indicated by the eigenvectors or the second steering vectors having a value greater than or equal to a threshold out of the calculated product or correlation. Furthermore, second position estimation unit 80 may estimate, as the number of living bodies, the number of the eigenvectors or the second steering vectors having a value greater than or equal to a threshold out of the calculated product or correlation. It should be noted that the threshold is for example 0.5, but may be determined as appropriate between a value greater than 0 and less than 1.

In the present embodiment, second position estimation unit 80 estimates the number and position of living bodies by calculating the correlation between second steering vectors $a_{peak}$ outputted by second steering vector output unit 60 and eigenvectors u calculated by eigenvector calculation unit 70.

Here, for example, second position estimation unit 80 may estimate the number of living bodies by using the evaluation function for calculating the correlation between second steering vectors $a_{peak}$ and eigenvectors u indicated in Equation 8.

[Math. 8]

$$P_{peaki} = \max[a_{peaki}^H u_1, a_{peaki}^H u_2, \ldots, a_{peaki}^H u_N]$$ Equation 8

In Equation 7, the correlations of second steering vectors $a_{peak}$ and eigenvectors u is calculated by calculating the inner products of second steering vectors $a_{peak}$ and eigenvectors u. As such, if there is an eigenvector u among the eigenvectors u having a high correlation with second steering vector $a_{peaki}$, the correlation becomes a value close to 1, otherwise the correlation becomes a value close to 0.

It should be noted that although computation for obtaining the maximum value for the correlation is performed in Equation 8, other computation such as summation may be substituted as long as it is possible to determine the presence or absence of an item having a correlation value close to 1.

Hereinafter, an example where the correlations between second steering vectors $a_{peak}$ and eigenvectors u are calculated by calculating the inner products of second steering vectors $a_{peak}$ and eigenvector u will be described with reference to FIG. 3.

FIG. 3 is a table showing an example of the result of calculating the correlations and evaluation functions of second steering vectors $a_{peak}$ and eigenvectors u according to Embodiment 1.

As illustrated in FIG. 3, the correlation between second steering vector $a_{peak1}$ and eigenvector $u_2$ indicated by reference sign 1101 is 0.9 which is a value that exceeds the threshold 0.5 and is close to 1. Furthermore, the correlation between second steering vector $a_{peak2}$ and eigenvector $u_1$ indicated by reference sign 1102 is 0.83 which is a value that exceeds the threshold 0.5 and is close to 1

Furthermore, based on the calculation results for the evaluation functions $P_{peaki}$ for second steering vectors $a_{peak1}$ to $a_{peakNp}$, the two evaluation functions $P_{peaki}$ indicated by reference signs 1103 and 1104 exceed the threshold 0.5. Accordingly, the estimated number of living bodies is two.

Specifically, as illustrated in FIG. 3, evaluation functions $P_{peaki}$ are calculated for the $N_P$ second steering vectors $a_{peak1}$ to $a_{peakNp}$ outputted by second steering vector output unit 60. Then, it is sufficient to count the number of evaluation functions $P_{peaki}$ exceeding the threshold 0.5, and output this number as the estimated number of living bodies. Furthermore, the peak positions corresponding to the evaluation functions $P_{peaki}$ exceeding the threshold 0.5 may be outputted as the estimated positions of the living bodies.

To describe this conceptually by associating FIG. 3 with FIG. 2, second steering vector $a_{peak1}$ corresponding to peak position 1001 becomes a value close to 0 because there is no eigenvector having a high correlation. In contrast, second steering vector $a_{peak2}$ corresponding to peak position 1002 becomes a value close to 1 because eigenvectors 1011-A and 1011-C having a high correlation are present. Furthermore, second steering vector $a_{peak3}$ corresponding to peak position 1003 also becomes a value close to 1 because eigenvectors 1011-B and 1011-D having a high correlation are present. Therefore, there are two evaluation functions $P_{peaki}$ exceeding the threshold, the number of living bodies is estimated to be two, and peak positions 1002 and 1003 corresponding to the evaluation functions $P_{peaki}$ exceeding the threshold are estimated to be the positions of the living bodies.

[Operation of Sensor 100]

The process of estimating the number of living bodies (living body count) performed by sensor 100 configured as described above will be described.

Figure 4:
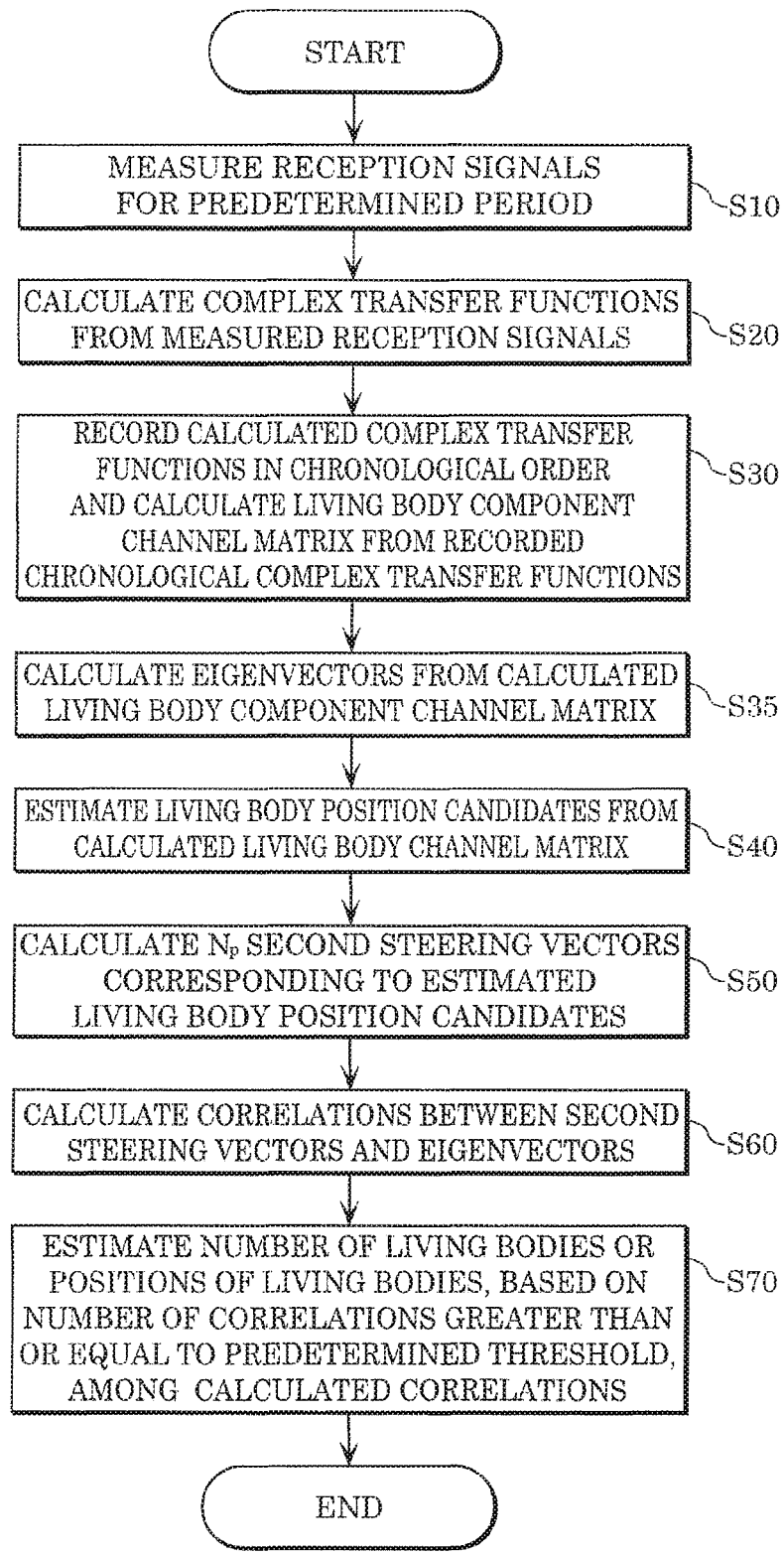
FIG. 4 is a flowchart illustrating a person count estimation process performed by the sensor according to Embodiment 1.

FIG. 4 is a flowchart illustrating the living body count estimation process performed by sensor 100 according to Embodiment 1.

First, as shown in FIG. 4, sensor 100 measures reception signals for a predetermined period using receiver 20 (S10), and calculates complex transfer functions from each of the measured reception signals (S20).

Next, sensor 100 records each of the calculated complex transfer functions in chronological order, and calculates a living body component channel matrix from the recorded chronological complex transfer functions (S30). Stated differently, sensor 100 extracts, from a reception signal obtained by receiving a signal transmitted to a predetermined space, living body information which is a component corresponding to one or more living bodies present in the predetermined space.

Next, sensor 100 calculates eigenvectors from the calculated living body component channel matrix (S35). Stated differently, sensor 100 calculates one or more eigenvectors of a living body correlation matrix obtained from the living body information.

Next, sensor 100 estimates living body position candidates using a position estimation method that can be used even when the person count is unknown, such as the Capon method, from the calculated living body component channel matrix (S40). Stated differently, sensor 100 estimates, according to a predetermined position estimation method, false image-inclusive positions of one or more living bodies, using the calculated living body correlation matrix.

Next, sensor 100 calculates $N_P$ second steering vectors corresponding to the estimated living body position candidates (S50). Stated differently, sensor 100 extracts and outputs, as second steering vectors, first steering vectors corresponding to the estimated false image-inclusive positions of the one or more living bodies, among the plurality of first steering vectors stored in advance in storage 50.

Next, sensor 100 calculates the correlations between the $N_P$ second steering vector and the eigenvectors (S60), and estimates the number of living bodies or the positions of the living bodies, based on correlations greater than or equal to a threshold among the correlations calculated in S60 (S70) Stated differently, sensor 100 selects one of the position or number of one or more living bodies, using eigenvectors and second steering vectors.

Effects, Etc

Estimation device 1, etc., according to the present embodiment can accurately estimate the number of living bodies present in a predetermined space, using radio signals. Furthermore, at the same time as estimating the number of living bodies, estimation device 1, etc., according to the present embodiment can estimate the corresponding living body positions.

More specifically, estimation device 1, etc., according to the present embodiment can improve person count estimation accuracy, by combining the two mutually different methods of a position estimation method that uses eigenvectors corresponding to eigenvalues and a predetermined position estimation method that can be used even when the person count is unknown, such as the Capon method.

With the method that uses eigenvalues, which is the existing living body count estimation method, when the signal-to-noise ratio is small, such as when the living body is located far, an eigenvalue corresponding to a living body and an eigenvector corresponding to noise are difficult to distinguish using a threshold. Although the orientation of an eigenvector corresponding to an eigenvalue is not easily affected by noise compared to an eigenvalue, use in person count estimation requires sorting according to the corresponding eigenvalue, and thus person count estimation cannot be performed using eigenvectors alone. In other words, when an eigenvalue is easily affected by noise, and the signal-to-noise ratio is small, person count estimation accuracy deteriorates.

In contrast, with the method that uses a position estimation method that can be used even when the person count is unknown, such as the Capon method, the possibility of an erroneous person count estimate is high because false images tend to be generated in the surroundings of the antenna, etc. Specifically, in the method which uses a position estimation method that can be used even when the person count is unknown, such as the Capon method, the position estimation method has poor position estimation accuracy, and the possibility of estimating that a living body is present at a position at which a living body is actually not present (that is, estimating a false image) is high, and thus, with this method alone, accurate person count estimation is not possible.

In view of this, in the present embodiment, person count estimation accuracy is improved by combining the two methods of the position estimation method that uses eigenvectors corresponding to eigenvalues, and a position estimation method such as Capon. Specifically, by associating calculated eigenvectors to vectors (steering vectors) associated to false image-inclusive estimated positions that have been calculated according to a predetermined position estimation method, it is possible to estimate estimated positions from which the false image has been removed. In this manner, it is possible to enhance the accuracy of estimated positions calculated according to a predetermined position estimation method, using information according to eigenvectors. Accordingly, it is possible to overcome the problems of both the method that uses eigenvalues which is an existing living body estimation method and a position estimation method that can be used even when the person count is unknown, such as the Capon method, and thus the number and positions of living bodies present in a predetermined space can be accurately estimated.

It should be noted that, in the present disclosure, in order to distinguish the false image included in the estimated image calculated according to the predetermined position estimation method, the correlations between the eigenvectors and the steering vectors are calculated as indices for quantitatively evaluating how probable each image is, and removing a false image. Accordingly, it is possible to realize an estimation method that is resistant to noise and has a wide detection range.

(Variation)

In the foregoing embodiment, using a position estimation method that can be used even when the person count is unknown, such as Capon, is used as a predetermined position estimation method was described, the position estimation method is not limited to this. A position estimation method based on the MUSIC method which assumes that the person count is known may be used. Hereinafter, this case will be described as a variation, centering on the points of difference with Embodiment 1.

Figure 5:
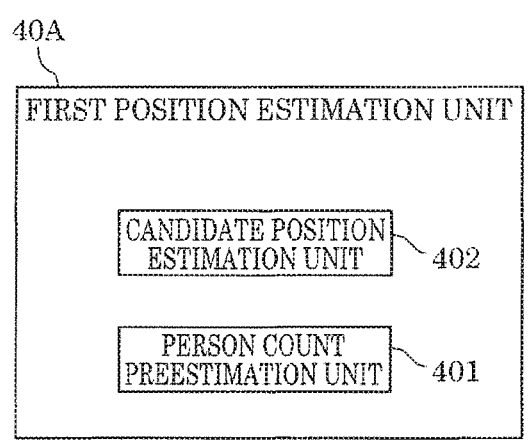
FIG. 5 is a block diagram illustrating a configuration of a first position estimation unit according to a variation of Embodiment 1.

FIG. 5 is a block diagram illustrating the configuration of first position estimation unit 40A according to a variation of Embodiment 1. As illustrated in FIG. 5, first position estimation unit 40A includes person count preestimation unit 401 and candidate position estimation unit 402.

Person count preestimation unit 401 estimates false-image inclusive number of persons (also referred to here as person count) of one or more living bodies, using the eigenvalues of a living body correlation matrix. In the present variation, before candidate position estimation unit 402 estimates the positions of living bodies which are the detection targets, person count preestimation unit 401 estimates the number of the living bodies which are the detection targets, using the eigenvalues obtained by eigenvector calculation unit 70 performing eigenvalue decomposition on correlation matrix R. Here, the person count estimated by person count preestimation unit 401 is the person count estimated for the time being using the eigenvalues, and is an inaccurate person count that includes one or more false images.

Candidate position estimation unit 402 estimates false image-inclusive candidate positions of one or more living bodies using, as the predetermined position estimation method, the MUSIC method which uses the person count estimated by person count preestimation unit 401. In the present variation, candidate position estimation unit 402 estimates candidate positions of living bodies 200 using the MUSIC method which uses, as an already-known person count, the inaccurate person count estimated by person count preestimation unit 401.

Accordingly, the estimation device, etc., according to the present variation can accurately determine at least the positions or the number of living bodies, using not only a position estimation method that can be used even when the person count is unknown, such as the Capon method, but also a position estimation method based on the MUSIC method in which the person count is already known.

Embodiment 2

In Embodiment 1, the case of estimating at least the positions or the number of living bodies using a single, that is, one sensor 100 is described. In Embodiment 2, the case of estimating at least the positions or the number of living bodies using two or more sensors 100 is described.

Hereinafter, a sensor including two or more sensors 100 will be referred to as compound sensor 101.

[Configuration of Compound Sensor 101]

Figure 6:
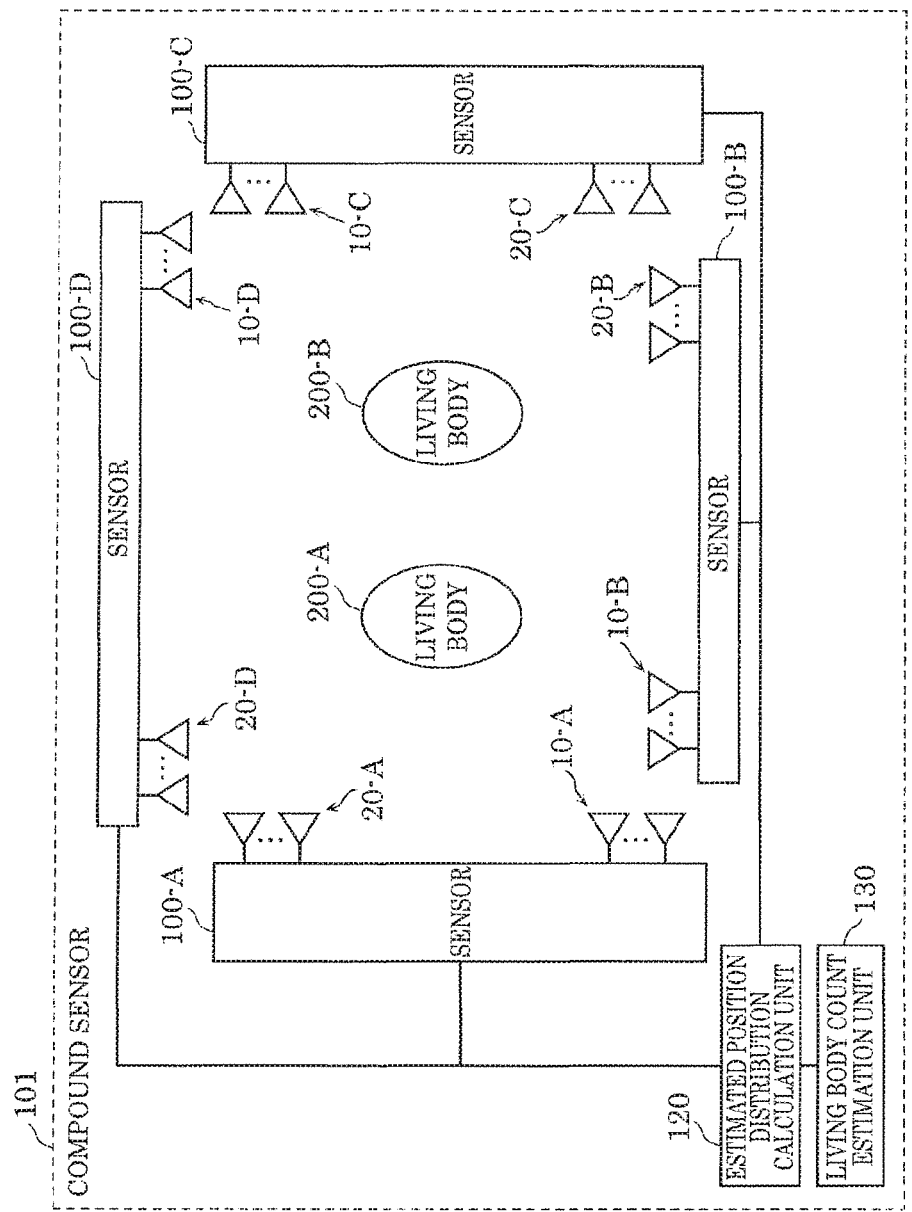
FIG. 6 is a block diagram illustrating a configuration of a compound sensor according to Embodiment 2.

FIG. 6 is a block diagram illustrating the configuration of compound sensor 101 according to Embodiment 2. The same numerical reference is given to constituent elements that are the same as those in FIG. 1 and their detailed description shall be omitted.

Compound sensor 101 is an example of a living body count estimation device, and includes a plurality of sensors 100 described in Embodiment 1. Compound sensor 101 estimates the positions and number of living bodies over a wider range and with higher accuracy by using the estimation results from the plurality of sensors 100. In the example illustrated in FIG. 6, compound sensor 101 includes sensor 100-A to sensor 100-D each of which is sensor 100, estimated position distribution calculation unit 120 and living body count estimation unit 130. It should be noted that, in FIG. 6, compound sensor 101 includes four sensors 100 for providing around a room (i.e., a predetermined space) in which a plurality of living bodies 200 (living bodies 200-A and 200-B) are present, but is not limited to such. The number of sensors 100 included in compound sensor 101 does not matter as long as there are two or more. Hereinafter, the detailed configuration will be described.

[Sensor 100-A to Sensor 100-D]

Each of sensor 100-A to sensor 100-D is sensor 100 described in Embodiment 1, and estimates the positions and the number of living bodies, using the radio signals transmitted and received between respective transmitters 10-A to 10D and respective receivers 20-A to 20-D. In the present embodiment, each of sensor 100-A to sensor 100-D estimates the number of living bodies 200 and the positions of living bodies 200. In addition, each of sensor 100-A to sensor 100-D outputs the estimated number of living bodies 200 and positions of living bodies 200 to estimated position distribution calculation unit 120.

[Estimated Position Distribution Calculation Unit 120]

Estimated position distribution calculation unit 120 calculates the estimated position distribution of a total space consisting of partially overlapping predetermined spaces, based on the positions of one or more living bodies 200 present in each of the predetermined spaces estimated by the plurality of sensors 100.

In the present embodiment, estimated position distribution calculation unit 120 receives the number (hereafter referred to as estimated person count) of living bodies 200 and the respective positions (hereafter referred to as estimated positions) of living bodies 200 estimated by each of sensor 100-A to sensor 100-D. Estimated position distribution calculation unit 120 calculates the estimated position distribution by plotting the received estimated person count and estimated positions on a plane or a space.

More specifically, estimated position distribution calculation unit 120 first specifies the coordinate system of the space which is the measurement range (referred to as total space), based on the predetermined spaces which are the respective measurement targets of sensor 100-A to sensor 100-D. Here, the predetermined spaces which are the respective measurement targets of sensor 100-A to sensor 100-D partially overlap and make up the total space. Then, estimated position distribution calculation unit 120 converts the total space which is the measurement range into a coordinate system, and plots the estimated positions outputted from each of sensor 100-A to sensor 100-D. It should be noted that estimated position distribution calculation unit 120 may overlappingly plot chronological data outputted from each of sensor 100-A to sensor 100-D and indicating the estimated positions estimated in a period of approximately several seconds in which living bodies 200 do not travel.

Figure 7A:
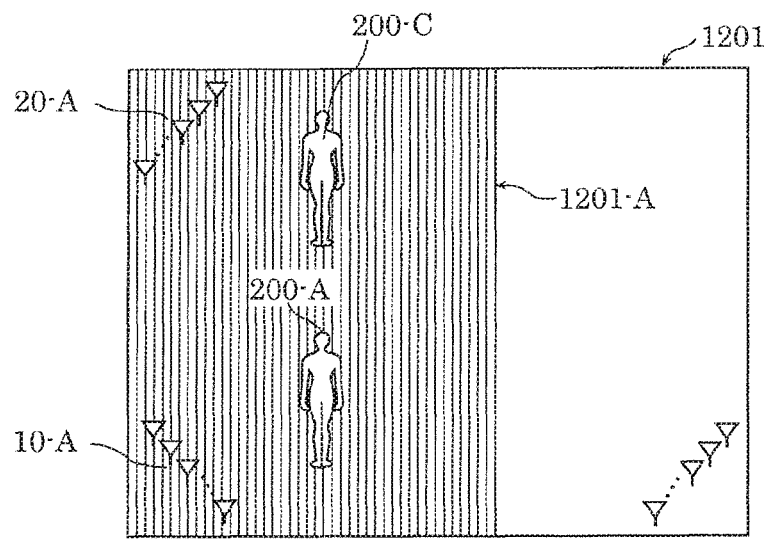
FIG. 7A is a conceptual diagram of an estimated position distribution calculated from the positions and person count estimated by a single sensor according to Embodiment 2.
Figure 7B:
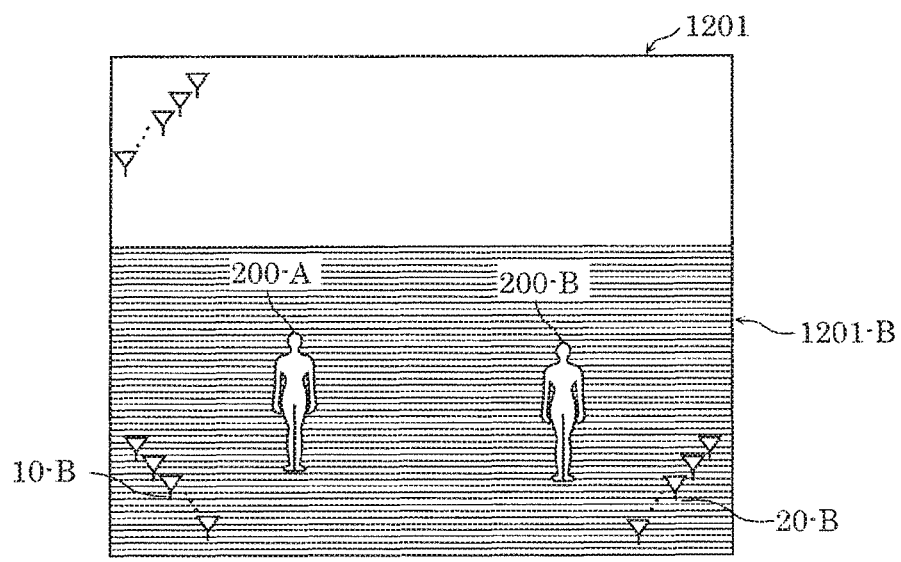
FIG. 7B is a conceptual diagram of an estimated position distribution calculated from the positions and person count estimated by a single sensor according to Embodiment 2.
Figure 8:
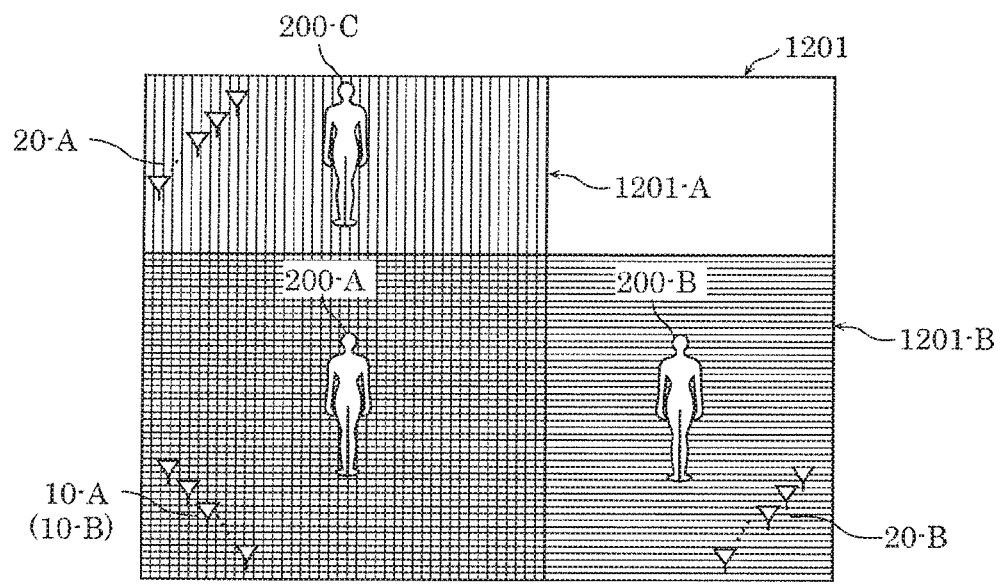
FIG. 8 is a conceptual diagram illustrating an example of an estimated position distribution calculated by an estimated position distribution calculation unit according to Embodiment 2.

Hereinafter, the concept of the estimated position distribution calculated by estimated position distribution calculation unit 120 will be described with reference to the drawings. FIG. 7A and FIG. 7B are conceptual diagrams of estimated position distributions calculated from the positions and person count estimated by a single sensor 100 according to Embodiment 2. FIG. 8 is a conceptual diagram illustrating an example of an estimated position distribution calculated by estimated position distribution calculation unit 120 according to Embodiment 2.

As illustrated in FIG. 7A, estimated position distribution calculation unit 120 for example converts total space 1201 which is the measurement range into a coordinate system, and plots the estimated positions of living body 200-A and living body 200-C in predetermined space 1201-A which is a measurement target, outputted from sensor 100-A. In the example, illustrated in FIG. 7A, predetermined space 1201-A makes up part of the area (left-side area) of total space 1201. In the same manner, as illustrated in FIG. 7B, estimated position distribution calculation unit 120 for example converts the coordinate system of total space 1201 which is the measurement range into a coordinate system, and plots the estimated positions of living body 200-A and living body 200-B in predetermined space 1201-B which is a measurement target, outputted from sensor 100-B. In the example illustrated in FIG. 7B, predetermined space 1201-B makes up part of the area (bottom-side area) of total space 1201.

Then, as illustrated in FIG. 8, estimated position distribution calculation unit 120 overlappingly plots the estimated positions of living bodies 200-A and 200-C in predetermined space 1201-A illustrated in FIG. 7A and the estimated positions of living bodies 200-A and 200-B in predetermined space 1201-B illustrated in FIG. 7B. In the example illustrated in FIG. 8, predetermined space 1201-A and predetermined space 1201-B partially overlap and are included in total space 1201.

It should be noted that, with regard to a living body that appears redundantly in the output from sensor 100-A and the output from sensor 100-B like living body 200-A illustrated in FIG. 8, living body count estimation unit 130 mathematically performs redundancy removal.

[Living Body Count Estimation Unit 130]

Living body count estimation unit 130 estimates the living body count which is the number of one or more living bodies present in the total space, using the number of one or more living bodies present in the respective predetermined spaces estimated by the plurality of sensors 100. Here, living body count estimation unit 130 may estimate, as the living body count, the number of local minimums of the dispersion of positions estimated by the plurality of sensors 100. Furthermore, living body count estimation unit 130 may estimate, as the living body count, the number of local maximums of the density of positions estimated by the plurality of sensors 100.

In the present embodiment, living body count estimation unit 130 performs person count estimation using the estimated position distribution calculated by estimated position distribution calculation unit 120. Specifically, living body count estimation unit 130 searches for the points of the local maximums of the density of the estimated position distribution, and estimates the number of the points as the number of living bodies 200. Furthermore, living body count estimation unit 130 may estimate the points of the local maximums as the positions of living bodies 200. In this manner, living body count estimation unit 130 can estimate the number of living bodies 200 present in the measurement range, after mathematically removing the number of living bodies plotted redundantly in the estimated position distribution calculated by estimated position distribution calculation unit 120.

It should be noted that the method of calculating the density of the estimated position distribution may be a method in which the space of the measurement range is partitioned into an appropriately sized grids, and the number of estimated positions plotted on each grid is counted, or a method which uses a reciprocal of the dispersion of a predetermined number of plotted points close to the center of each grid. However, it is sufficient to select, from among the local maximums of the density of the estimated position distribution, a local maximum having a value that is greater than or equal to a threshold. Accordingly, it is possible to prevent a misestimation in the case where there is no living body 200, that is, in the case where there are no people in the measurement range.

It should be noted that, living body count estimation unit 130 may search for the points of the local minimums of the density of the estimated position distribution, and estimate the number of the points as the number of living bodies 200

[Operation of Compound Sensor 101]

The process of estimating the number of living bodies (living body count) performed by compound sensor 101 configured as described above will be described.

Figure 9:
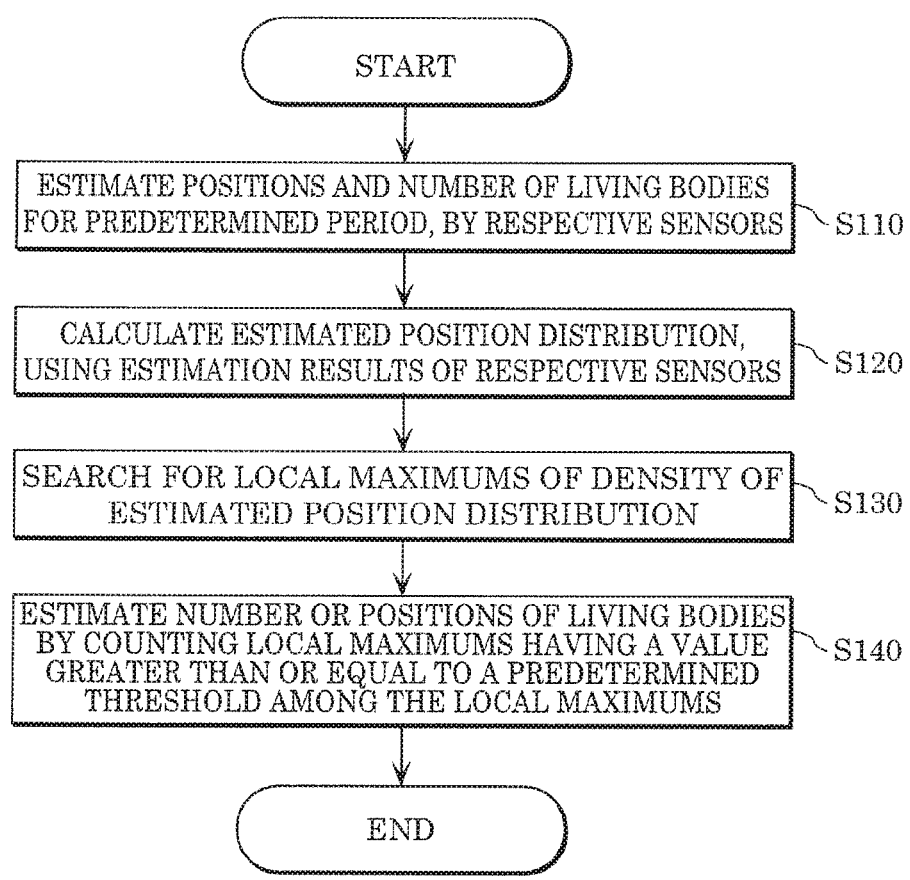
FIG. 9 is a flowchart illustrating a person count estimation process performed by the compound sensor according to Embodiment 2.

FIG. 9 is a flowchart illustrating the living body count estimation process performed by compound sensor 101 according to Embodiment 2.

First, as illustrated in FIG. 9, compound sensor 101 causes each of sensors 100 (sensor 100-A to sensor 100-D) to estimate the positions and the number of living bodies for a predetermined period (S110).

Next, compound sensor 101 calculates the estimated position distribution using the estimation results of respective sensors 100 (S120). More specifically, compound sensor 101 calculates the estimated position distribution by overlappingly plotting, on the total space which is to be the measurement range, the estimated number and positions of persons outputted by respective sensors 100.

Next, compound sensor 101 searches for the local maximums of the density of the estimated position distribution calculated in S120 (S130). It should be noted that compound sensor 101 may search for the local minimums of the dispersion of the estimated position distribution calculated in S120.

Lastly, compound sensor 101 estimates the number or the positions of living bodies by counting the number of local maximums having a value greater than or equal to a threshold among the local maximums searched out in S130 (S140). More specifically, compound sensor 101 estimates, as the number of living bodies, the number of local maximums that are greater than or equal to a threshold, among the local maximums searched out in S130. Furthermore, living body count estimation unit 130 estimates, as the positions of the living bodies, the points of the local maximums searched out in S130. It should be noted that compound sensor 101 may estimate the living body count or living body positions by counting the number of local minimums searched out in S130.

Effects, Etc

Compound sensor 101, etc., according to Embodiment 2 can accurately estimate the number of living bodies present in a measuring range by using radio signals. More specifically, aside from the advantageous effect obtained by sensor 100, etc., according to Embodiment 1, compound sensor 101 according to Embodiment 2 can cause a plurality of sensor 100 to operate together and thus can accurately estimate the positions and the number of living bodies. In other words, compound sensor 101 according to Embodiment 2 can accurately estimate the number of living bodies in a measurement range made up of a plurality of predetermined ranges, which is wider than a predetermined space which is the measurement range of each of sensors 100. For this reason, even when there is a metal obstruction in the measurement range of a particular sensor 100 and radio wave reception condition is poor, compound sensor 101 according to Embodiment 2 can reduce the blind area in the measurement range by causing another sensor 100 to operate together, and thus can accurately estimate the number of living bodies.

Working Example

Here, evaluation according to an experiment for verifying the advantageous effects according to Embodiment 2 has been performed and is described below as a working example.

Figure 10:
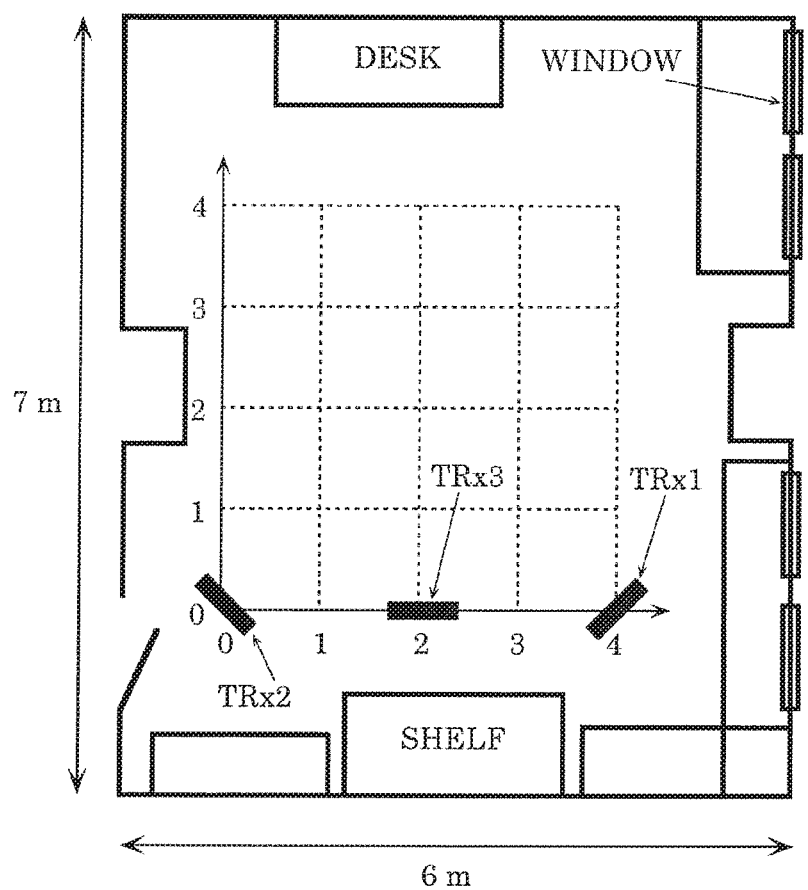
FIG. 10 is a diagram illustrating the environment of an experiment using the estimation method according to Embodiment 2.

FIG. 10 is a diagram illustrating the environment in which an experiment was performed using the estimation method according to Embodiment 2.

This experiment was carried out with living bodies standing at three locations, (0.5, 2), (2, 2), and (3.5, 2), in a room that is 6 meters wide and 7 meters long. Furthermore, in this experiment, 4-element linear array antennas are used in transmission and reception stations denoted by TRx1 to TRx3 in FIG. 10. It should be noted that TRx1 to TRx3 correspond to the transmission and reception array antennas included in transmission antenna unit 12 and reception antenna unit 21 included in sensor 100. Furthermore, in this experiment transmission and reception stations TRx1 to TRx3 are placed at coordinates (0, 0), (2, 0), and (4, 0). Furthermore, the transmission and reception array elements included in the 4-element linear array antennas used in transmission and reception stations TRx1 to TRx3 have an interval of 0.5 wavelengths, a use frequency of 2.47125

GHz, a sampling frequency of 100 Hz, and the frequency range of the living body activity to be extracted is set to 0.3 to 3.3 Hz.

Figure 11A:
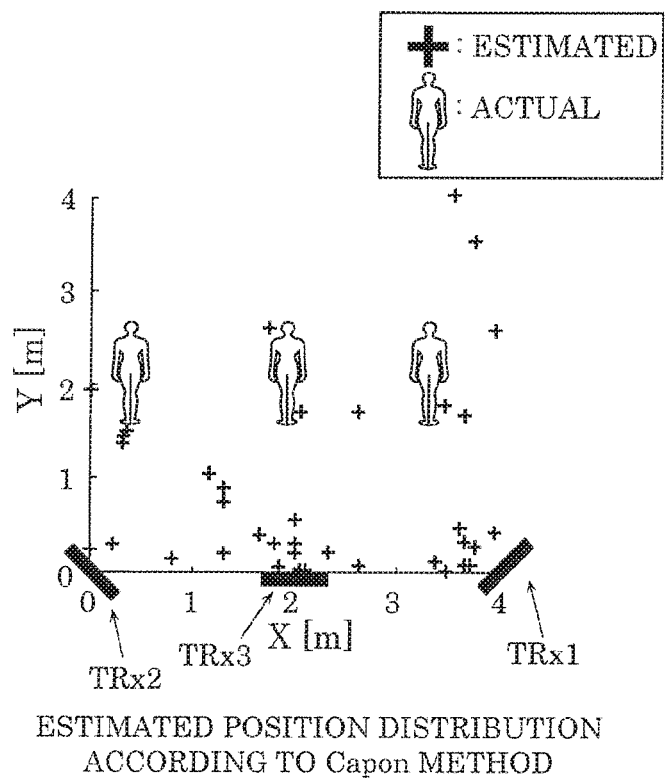
FIG. 11A is a diagram illustrating an estimated position distribution according to the Capon method.
Figure 11B:
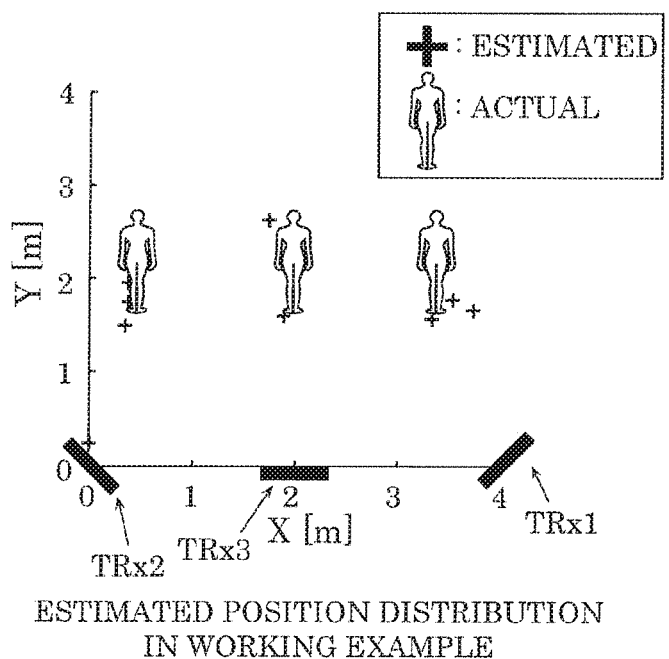
FIG. 11B is a diagram illustrating an estimated position distribution according to a working example.

FIG. 11A is a diagram illustrating the estimated position distribution according to the Capon method, and FIG. 11B is a diagram illustrating the estimated position distribution in the present working example. In FIG. 11A and FIG. 11B, illustrations of persons are rendered at positions of real images where living bodies are actually present.

FIG. 11A illustrates the result when position estimation of living bodies is performed in the room illustrated in FIG. 10 using only the Capon method. It should be noted that although items of chronological data indicating the estimated positions ("+" in the figure) estimated during periods of about several seconds in which a living body is not travelling are overlappingly plotted in FIG. 11A, estimated positions estimated only once may be plotted. Furthermore, FIG. 11B illustrates the superimposition of results, that is, the estimated position distribution, when position estimation of living bodies is performed in the room illustrated in FIG. 10, according to the working example which combines the two mutually different estimation methods of the Capon method and a method which uses eigenvectors.

As can be seen by comparing FIG. 11A and FIG. 11B, the estimated positions ("+" in the figure) other than those near the positions where a person is rendered are reduced in FIG. 11B. In other words, it can be understood that many false images generated in the Capon method were removed in the method of the present working example which combines a position estimation method such as the Capon method and a method which uses eigenvalues.

Figure 12:
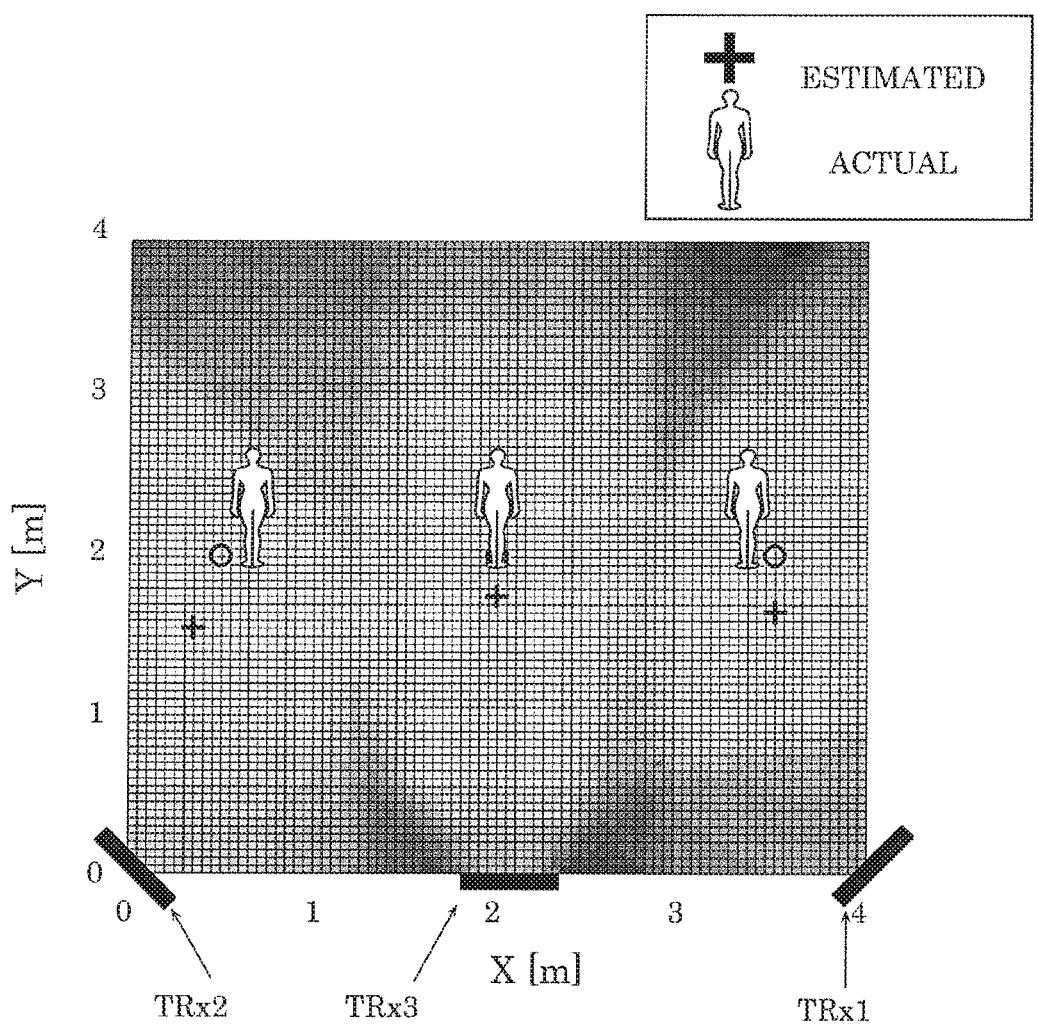
FIG. 12 is a diagram illustrating a spectrum indicating the dispersal of the estimated position distribution illustrated in FIG. 11B.

FIG. 12 is a diagram illustrating a spectrum indicating the dispersal of the estimated position distribution illustrated in FIG. 11B.

As illustrated in FIG. 12, in the working example, the spectrum indicating the dispersal of the estimated position distribution illustrated in FIG. 11B is calculated, and the local maximums of the densities of the estimated position distribution is searched for. As illustrated in FIG. 12, since the number of local maximums ("+" in the figure) is three, the number of living bodies can be correctly estimated as three. Accordingly, it can be understood that, by searching for the local maximums of the density of the estimated position distribution, the same living body estimated overlappingly by a plurality of estimation devices can be counted as one living body.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The present disclosure can be used in an estimation device, etc., which estimates at least the positions or the number of living bodies using radio signals, and can be used in particular in a measuring device that measures the number or the positions of living bodies, a household appliance that performs control according to the number or the positions of living bodies, or a monitoring device that detects incursion of a living body, and so on.

What is claimed is:

1. An estimation device, comprising:
a living body information extraction unit configured to extract, from a reception signal obtained by receiving a signal transmitted to a predetermined space, living body information which is a component corresponding to one or more living bodies present in the predetermined space;
an eigenvector calculation unit configured to calculate one or more eigenvectors of a living body correlation matrix obtained from the living body information;
a first position estimation unit configured to estimate, using the living body correlation matrix, positions including a position of each of the one or more living bodies and a position of at least one false image, according to a predetermined position estimation method;
a second steering vector output unit configured to extract, from among a plurality of first steering vectors stored in advance in a storage, first steering vectors corresponding to the positions estimated by the first position estimation unit, and output the first steering vectors as second steering vectors; and
a second position estimation unit configured to estimate at least one of the position of each of the one or more living bodies and a total number of the one or more living bodies, using the one or more eigenvectors and the second steering vectors.

2. The estimation device according to claim 1, wherein the second position estimation unit is configured to calculate a product or a correlation of the one or more eigenvectors and the second steering vectors, and estimate, as the position, a position indicated by eigenvectors or second steering vectors of which the product or the correlation calculated is a value greater than or equal to a threshold, among the one or more eigenvectors and the second steering vectors.

3. The estimation device according to claim 1, wherein the second position estimation unit is configured to estimate, as the total number, a total number of eigenvectors or second steering vectors of which the product or the correlation calculated is a value greater than or equal to a threshold, among the one or more eigenvectors and the second steering vectors.

4. The estimation device according to claim 1, wherein the predetermined position estimation method is a Capon method.

5. The estimation device according to claim 1, wherein the predetermined position estimation method is a Beamformer method.

6. The estimation device according to claim 1, wherein the first position estimation unit includes an advance person count estimation unit configured to estimate a person count including the total number of the one or more living bodies and a total number of the at least one false image, using eigenvalues of the living body correlation matrix, and
the predetermined position estimation method is a multiple signal classification (MUSIC) method that uses the person count estimated by the advance person count estimation unit.

7. The estimation device according to claim 1, further comprising:
a transmitter including N transmission antenna elements, where N is a natural number greater than or equal to 2; and
a receiver including M reception antenna elements, where M is a natural number greater than or equal to 2, and a transfer function calculation unit configured to calculate, from reception signals received by each of the M reception antenna elements during a predetermined period, a plurality of complex transfer functions indicating a propagation characteristic between the N transmission antenna elements and the M reception antenna elements, wherein the living body information extraction unit is configured to extract, as the living body information, a variation component in each of the M reception antenna elements, from the plurality of complex transfer functions calculated by the transfer function calculation unit, the variation component resulting from influence of the one or more living bodies, and the eigenvector calculation unit is configured to calculate the living body correlation matrix from the variation component in each of the M reception antenna elements extracted by the living body information extraction unit, and calculate the one or more eigenvectors of the living body correlation matrix calculated.

8. A living body count estimation device, comprising:
a plurality of estimation devices each being the estimation device according to claim 1;
an estimated position distribution calculation unit configured to calculate, based on a position of each of one or more living bodies present in each of predetermined spaces that is estimated by a corresponding one of the plurality of estimation devices, an estimated position distribution for a total space including the predetermined spaces which partially overlap each other; and
a living body count estimation unit configured to estimate a living body count which is a total number of one or more living bodies present in the total space, using the total number of the one or more living bodies present in each of the predetermined spaces estimated by the corresponding one of the plurality of estimation devices.

9. The living body count estimation device according to claim 8, wherein
the living body count estimation unit is configured to estimate, as the living body count, a total number of local minimums of a dispersal of the positions estimated by the plurality of estimation devices.

10. The living body count estimation device according to claim 8, wherein
the living body count estimation unit is configured to estimate, as the living body count, a total number of maximum values of a density of the positions estimated by the plurality of estimation devices.

11. An estimation method, comprising:
extracting, from a reception signal obtained by receiving a signal transmitted to a predetermined space, living body information which is a component corresponding to one or more living bodies present in the predetermined space;
calculating one or more eigenvectors of a living body correlation matrix obtained from the living body information;
estimating, using the living body correlation matrix, positions including a position of each of the one or more living bodies and a position of at least one false image, according to a predetermined position estimation method;
extracting, from among a plurality of first steering vectors stored in advance in a storage, first steering vectors corresponding to the positions estimated in the estimating of the positions, and outputting the first steering vectors as second steering vectors; and
estimating at least one of the position of each of the one or more living bodies and a total number of the one or more living bodies, using the one or more eigenvectors and the second steering vectors.

12. A non-transitory computer-readable recording medium having recorded thereon a program for causing a computer to execute:
extracting, from a reception signal obtained by receiving a signal transmitted to a predetermined space, living body information which is a component corresponding to one or more living bodies present in the predetermined space;
calculating one or more eigenvectors of a living body correlation matrix obtained from the living body information;
estimating, using the living body correlation matrix, positions including a position of each of the one or more living bodies and a position of at least one false image, according to a predetermined position estimation method;
extracting, from among a plurality of first steering vectors stored in advance in a storage, first steering vectors corresponding to the positions estimated in the estimating of the positions, and outputting the first steering vectors as second steering vectors; and
estimating at least one of the position of each of the one or more living bodies and a total number of the one or more living bodies, using the one or more eigenvectors and the second steering vectors.

* * * * *